United States Patent [19]

Carmosin et al.

[11] Patent Number: 4,716,172

[45] Date of Patent: Dec. 29, 1987

[54] 4-SUBSTITUTED OCTAHYDROQUINOLIZINE ANALGESIC COMPOUNDS AND OCTAHYDROQUINOLIZINIUM INTERMEDIATES

[75] Inventors: Richard J. Carmosin, Quakertown; John R. Carson, Norristown, both of Pa.

[73] Assignee: McNeilab, Inc., Spring House, Pa.

[21] Appl. No.: 850,631

[22] Filed: Apr. 10, 1986

[51] Int. Cl.$^4$ .................. A61K 31/345; C07D 455/02
[52] U.S. Cl. ...................................... 514/306; 546/138
[58] Field of Search ........................ 546/138; 514/306

[56] References Cited

U.S. PATENT DOCUMENTS 4,582,836  4/1986  Carmosin et al. .................... 546/121

FOREIGN PATENT DOCUMENTS 1096589  12/1967  United Kingdom ................ 546/138

OTHER PUBLICATIONS

"Constituents of Rhizoma Nupharis . . . ", Chem. Pharm. Bull., vol. 27, No. 10, pp. 2456–2462, Shingo Yasuda et al., 1979.
"Synthese und Konfigurationsbestimmung . . . ", Chemische Berichte, vol. 94, No. 12, pp. 3151–3165, Ferdinand Bohlmann et al., 1961.
"Constituents of Rhizoma Nupharis . . . ", Chem. Pharm. Bull., vol. 16, No. 10, pp. 2074–2077, Yoshio Arata, 1968.
"Über Die Dehydrierung . . . ", Tetrahedron Letters, No. 3, pp. 167–170, F. Bohlmann et al., 1965.
"Curariform Activity and Chemical Structure . . . ", pp. 5005–5009, V. Boekelheide et al., Nov. 1950.
"NMR-Spektren Von Chinolizidin-Derivaten: . . . ", Tetrahedron Letters, No. 31, pp. 2705–2711, Ferdinand Bohlmann, 1965.
"Synthetic Studies on Lythraceae Alkaloids . . . ", Chem. Pharm. Bull., pp. 1045–1049, vol. 24, No. 5, Miyoji Hanaoka, 1976.
"Total Synthesis of (±)-Vertaline", Chem. Pharm. Bull., vol. 22, No. 4, pp. 973–974, Miyoji Hanaoka et al., 1974.
"Synthesis of (±)-Desmethyldecaline", Chem. Pharm. Bull., vol. 22, No. 8, pp. 1945–1946, Miyoji Hanaoka et al., 1974.
"Intramolecular Michael Additions in the Pelletierine-Benzaldehyde Condensation", Tetrahedron Letters, No. 7, pp. 603–606, James Quick et al., 1977.
"3-Arylquinolizidines, Potential Antidepressant Agents", J. Med. Chem., vol. 18, No. 11, pp. 1126–1130, M. E. Rogers et al., 1975.

*Primary Examiner*—Henry R. Jiles
*Assistant Examiner*—J. Richter
*Attorney, Agent, or Firm*—David J. Levy

[57] ABSTRACT

Octahydroquinolizine and corresponding octahydroquinolizinium compounds of formulae (I) and (Va):

where A is a 3 to 7 membered carbocyclic ring, $R^1$ is a substituent, n is 0–2, x is 0–3, and Y is an anion. Also, pharmaceutical compositions for treating pain containing (I) and methods for synthesis and use as well as novel intermediates in the synthesis.

20 Claims, No Drawings

4-SUBSTITUTED OCTAHYDROQUINOLIZINE ANALGESIC COMPOUNDS AND OCTAHYDROQUINOLIZINIUM INTERMEDIATES

The present invention comprises certain octahydroquinolizine compounds including acid addition salts thereof, methods for their preparation and use, pharmaceutical compositions and intermediates used in their synthesis.

Quinolizines with various substituents including phenyl and substituted phenyl are disclosed by S. Yasuda et al in Chem. Pharm. Bull. Vol. 27, pages 2456–2462 (1979); by F. Bohlmann et al in Chem. Ber., Vol. 94, No. 12, pages 3151–3156 (1961); S. Yasuda et al. in Chem. Pharm. Bull., Vol. 16, pages 2074–2077 (1968); F. Bohlmann et al. in Tet. Let., No. 3, pages 167–170 (1965); and by V. Boekelheide et al in JACS Vol 72. pages 5005–5009 (1950).

SUMMARY OF THE INVENTION

Invention compounds are of the following formula (I):

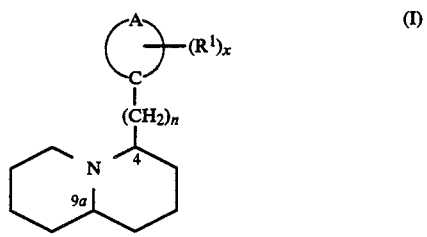

and acid addition salts wherein A represents the atoms necessary to form a 3 to 7 membered carbocyclic ring or an aromatic ring, n is 0–2, $R^1$ is a substituent and x is 0–3. Also included within the invention are pharmaceutical compositions, methods for the synthesis of formula (I) compounds and intermediates used in such synthesis, in particular those of formula (Va).

DETAILED DESCRIPTION OF THE INVENTION

Compounds of the present invention are octahydroquinolizines of the following formula (I):

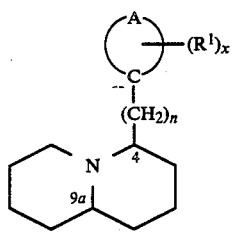

wherein
A represents the atoms necessary to form a phenyl, naphthyl, cycloalkyl, or cycloalkenyl ring system as the A-C cycle shown in formula (I):
$R^1$ is independently cyano; halogen; alkyl; alkoxy; phenoxy; alkylthio; phenylthio; phenylthio substituted by acetamido, halo, or alkyl; haloalkyl; alkenyl; alkynyl or cycloalkenyl;
n is the integer 0, 1, or 2; and,
x is the integer 0, 1, 2, or 3, provided that when A is phenyl and n is 0, x is 1, 2, or 3; and, when A is phenyl, n is 0, x is 1, and $R^1$ is methoxy, $R^1$ is in the 2- or 3-position of the phenyl ring.
and the pharmaceutically-acceptable acid-addition salts thereof.

Pharmaceutical compositions of the invention comprise the formula (I) compounds as defined above also including those wherein when A is phenyl, n is 0 and x is 0; and, when A is phenyl, n is 0, x is 1, and $R^1$ is methoxy in the 4-position of said phenyl ring, and methods for the use of such pharmaceutical compositions.

In more detail, A is phenyl; naphthyl; cycloalkyl of about 3 to 7 carbons such as cyclopentyl and cyclohexyl; or cycloalkenyl of about 3 to 7 carbons such as cyclopentenyl and cyclohexenyl, e.g. 1-cyclohexen-1-yl.

$R^1$, in more detail, is independently e.g., two different $R^1$ moieties may be attached to the A ring when x is 2, cyano; halogen such as fluoro, chloro, bromo and iodo; alkyl of about 1 to 8 carbons such as methyl, ethyl, n-propyl and sec-butyl; alkoxy of about 1 to 8 carbons such as methoxy, ethoxy and iso-propoxy; phenoxy; alkylthio of about 1 to 8 carbons such as methylthio and ethylthio; phenylthio; phenylthio substituted by a single moiety of acetamido, fluoro, chloro, bromo, iodo, or alkyl of about 1 to 6 carbons such as methyl and ethyl, such substitution being at the o-, m-, or p-position, most particularly at the p-position; haloalkyl of about 1 to 8 carbons independently substituted by one or more of fluoro, chloro, bromo, or iodo such as trifluoromethyl and 2,2,2-trifluoroethyl; alkenyl of about 2 to 8 carbons such as ethenyl, 1-propenyl and 2-propenyl; alkynyl of about 2 to 8 carbons such as ethynyl, 1-propargyl and 2-propargyl; or cycloalkenyl of about 3 to 7 carbons such as cyclopropenyl and 1-cyclohexenyl.

n is an integer from 0–2, preferably 0.

x is an integer from 0–3, provided that when A is phenyl and n is 0, x is 1, 2, or 3; and, when A is phenyl, n is 0, x is 1, and $R^1$ is methoxy, $R^1$ is in the 2-, 3-, or 5-position of said phenyl ring.

Particular A-$R^1$ ring systems for formula (I) include phenyl rings where x is 1, 2, or 3 and at least one $R^1$ is ortho; phenyl rings where x is 1–3 and $R^1$ is halogen such as ortho-halophenyl, e.g., ortho-bromophenyl and ortho-iodophenyl; 2,6-dichlorophenyl, para-phenoxyphenyl and meta-methoxyphenyl; and phenyl rings where n is 0, 1 or 2.

Particular invention compounds of formula (I) shown in the Examples include the following:
4-(2,6-dichlorophenyl)octahydro-2H-quinolizine;
octahydro-4-(4-phenoxyphenyl)-2H-quinolizine;
octahydro-4-(3-methoxyphenyl)-2H-quinolizine;
octahydro-4-(2-iodophenyl)-2H-quinolizine; and
4-(2-bromophenyl)octahydro-2H-quinolizine.

Various isomers are possible in the compounds of the invention, e.g. the formula (I) compounds, and the present invention includes all such individual enantiomers, diasteromers, racemates and other isomer ratios. Specifically such compounds may exist in the following forms: trans racemic, trans (+), trans (−), cis racemic, cis (+), and cis (−). Optical isomers of the compounds of this invention may be obtained by conventional resolution techniques known to those skilled in the art of organic chemistry. For example, addition of an optically active acid, eg (+) or (−) tartaric acid, (+) or (−) camphor sulfonic acid, (+) or (−) mandelic acid or (+) or (−) p-toluoyltartaric acid to the free base of the compounds of this invention to produce a mixture of two diastereomeric salts. Separation of the diastereomeric salts by conventional methods such as fractional crystallization and liberation of the free bases from the individual salts provides the individual enantiomeric free bases.

Resolution of enantiomers, of course, results in a single enantiomer without its enantiomeric mirror image and these individual enantiomers are designated by (−) or (+) according to the direction in which they rotate polarized light. When used in the present application, a "trans" compound is one wherein the 4-position—$(CH_2)_n$—substituent and 9a hydrogen are trans to each other, e.g. the racemate or either enantiomer. Thus, in the trans molecule, the hydrogens at the 4 and 9a position are cis to each other. In the reaction sequences described in the examples, the trans compound is somewhat easier to isolate and usually is recovered first by flash chromatography on silica gel. However, the cis compound is produced and may be isolated by standard recovery techniques.

Representative salts of the compounds of formulae (I) which may be used include those made with acids such as hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, cinnamic, mandelic, methanesulfonic, ethanesulfonic, hydroxyethane-sulfonic, benezenesulfonic, p-toluene sulfonic, cyclo-hexanesulfamic, salicylic, p-aminosalicylic, 2-phenoxy-benzoic, 2-acetoxybenzoic or a salt made with saccharin. Such salts can be made by reacting the free base of (I) with the acid and recovering the salt. Also within the scope of the invention are the various hydrate and solvate forms of the compounds of formulae (I) and (Va).

Compounds of this invention may be prepared via the route shown in the following Reaction Scheme.

Reaction Scheme:

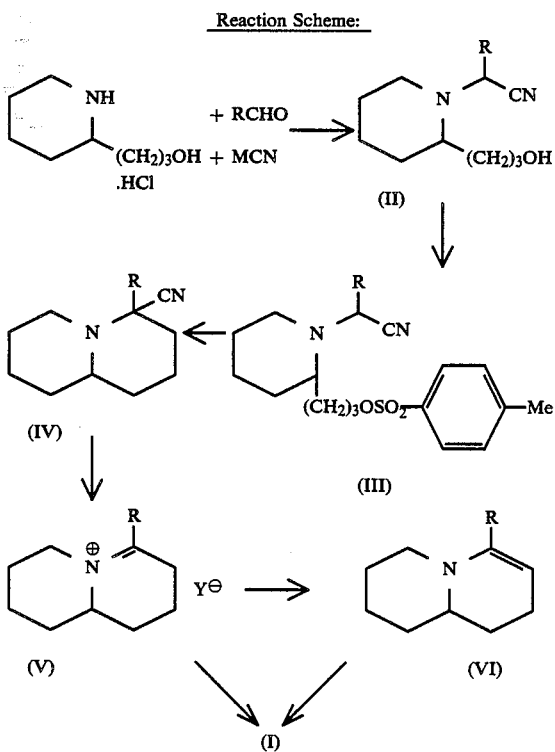

According to the above Reaction Scheme, an aldehyde RCHO wherein R is —$(CH_2)_n$—C—A($R^1$)$_x$ is added to an aqueous solution of 3-(2-piperidine)-1-propanol hydrochloride in the presence of a cyanide salt of the formula MCN wherein M represents an alkali metal cation such as sodium or potassium, to produce a hydroxypropyl piperidine of formula (II). The hydroxypropyl piperidine of formula (II) is then caused to react with p-toluene-sulfonyl chloride in a solvent such as pyridine or triethylamine/methylene chloride at a temperature of about −50° C. to about 25° C. to produce a piperidine propylsulfonate of formula (III). The propylsulfonate of formula (III) is then cyclized by the action of a strong base such as sodium hydride, sodamide, lithium diethylamide, potassium t-butoxide, or sodium hexamethyldisilazide in a polar aprotic solvent such as N,N-dimethylformamide at a temperature of about 0° C. to about 50° C. to produce a cyano quinolizine of formula (IV). The cyano quinolizine of formula (IV) is then treated with concentrated aqueous perchloric acid or other acids such as tetrafluoroboric or trifluoromethane sulfonic in a solvent such as ethanol, methanol or water at a temperature of about 20° C. to about 100° C. for a period of about one hour to several days to produce an octahydroquinolizinium salt of formula (V). Y is an anion such as perchlorate, tetrafluoroborate and trifluoromethanesulfonate. The octahydroquinolizinium salt of formula (V) is then reduced by a catalytic or hydride reducing agent to produce the octahydroquinolizine compounds of formula (I). When a hydride reducing agent is used, such as sodium cyanoborohydride or sodium borohydride, a solution of the octahydroquinolizinium salt of formula (V) in a solvent such as methanol, or alternatively lithium aluminum hydride in an ether-like solvent, such as diethyl ether or tetrahydrofuran, is treated with the hydride reducing agent. In the case where sodium cyanoborohydride is used as the reducing agent, methanolic hydrogen chloride is added to adjust the pH of the reaction mixture to about pH 3. The resulting reaction mixture is stirred at a temperature of about 20° C. to about 30° C. for a period of about 5 to 50 hours. The octahydroquinolizine of formula (I) is then isolated and purified by methods known to those skilled in the art of organic chemistry, such as acid/base extraction followed by crystallization of the free base or an acid addition salt or chromatographic procedures. When a catalytic reduction procedure is used, the isomeric free base of the octahydroquinolizinium perchlorate of formula (V), i.e., the hexahydroquinolizine of formula (VI), is generated by standard base extraction procedures known to those skilled in the art of organic chemistry. The hexahydroquinolizine of formula (VI) is then reacted with hydrogen under a pressure of about 16 to about 200 psi at a temperature of about 20° C. to about 50° C. in a solvent such as glacial acetic acid or ethanol in the presence of a catalyst such as platinum oxide, rhodium, or palladium, provided halogen is not present in the ring, to produce the octahydoquinolizine of formula (I).

A compound of type (I) where the A-ring is phenyl and $R^1$ is halo may be transformed to other derivatives, for instance to a substituted phenylthio derivative by treatment with an arylthiol in the presence of base and a palladium (O) catalyst.

The groups $R^1$ may be attached directly to the —C-A function during the synthesis of the octahydroquinolizine ring. Alternatively they may be attached following the synthesis of a 4-substituted octahydroquinolizine. For instance a 4-(halophenyl)octahydroquinolizine may be converted to the corresponding lithium derivative by reaction with an alkyllithium. 4-(2-Lithiophenyl)-octahydroquinolizine on reaction with dimethyldisulfide affords 4-(2-methylthiophenyl)octahydroquinolizine. Reaction of the lithio derivative with cyclohexanone affords the 1-cyclohexanol derivative which can be dehydrated to a cycloalkene. A 4-(2-halo-phenyl)octahydroquinolizine, when subjected to palladium catalyzed coupling with cuprous cyanide or a 1-alkyne gives the corresponding cyano or alkynyl derivative. Compounds of formula (I) wherein the A-ring is cyclohexyl or substituted cyclohexyl may be prepared by catalytic hydrogenation of the appropriate phenyl compound over a noble metal catalyst, for example rhodium, ruthenium or platinum, provided, however, that such hydrogenation cannot be carried out when a sulphur atom is present in the molecule.

Also within the scope of the invention are novel intermediates used in the Reaction Scheme above, e.g. formulae (II), (III), (IV), (V) and (VI). In particular, the invention includes formula (V) compounds shown in more detail as (Va) below, and the cation portion of formula (V) wherein $Y^-$ is an anion, e.g. a pharmaceutically-acceptable anion as described for formula (I) salts or other anions such as perchlorate, tetrafluoroborate, or trifluoromethanesulfonate, and particularly perchlorate, and the isomeric considerations described herein for formula (I). Formula (Va) is as follows:

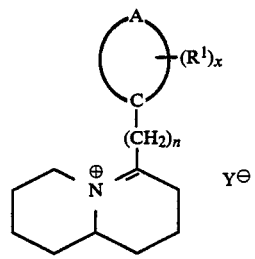

(Va)

where A, $R^1$, x and n are as defined for formula (I) and Y is as defined for formula (V).

Particular invention compounds of formula (Va) shown in the examples are the following:

4-(2,6-dichlorophenyl)-1,2,3,6,7,8,9,9a-octahydroquinolizinium perchlorate;

4-octahydro-(4-phenoxyphenyl)-1,2,3,6,7,8,9,9a-quinolizinium perchlorate;

4-(3-methoxyphenyl)-1,2,3,6,7,8,9,9a-octahydroquinolizinium perchlorate;

4-octahydro-(2-iodophenyl)-1,2,3,6,7,8,9,9a-quinolizinium perchlorate; and 4-(2-bromophenyl)-1,2,3,6,7,8,9,9a-octahydroquinolizinium perchlorate.

The activity of compounds (I) of the invention as analgesics may be demonstrated by an abdominal constriction assay as described below:

Mouse Acetylcholine-Bromide-Induced Abdominal Constriction Assay:

The mouse acetylcholine-induced abdominal constriction assay, as described by Collier et al. in Brit. J. Pharmacol. Chem. Ther., 32:295–310, 1968, with minor modifications was the test used to assess analgesic potency. The test drugs or appropriate vehicle were administered orally (p.o.) and 30 minutes later the animals received an intraperitoneal (i.p.) injection of 5.5 mg/kg acetylcholine bromide (Matheson, Coleman and Bell, East Rutherford, NJ). The mice were then placed in groups of four into glass bell jars and observed for a ten minute observation period for the occurrence of a writhe (defined as a wave of constriction and elongation passing caudally along the abdominal wall, accompanied by a twisting of the trunk and followed by extension of the hind limbs). The percent inhibition of writhing (equated to % analgesia) was calculated as follows: The % inhibition of writhing, i.e., % analgesia, is equal to the difference between the No. of control animals writhing and the No. of drug-treated animals writhing times 100 divided by the No. of control animals writhing.

At least 20 animals were used for control and in each of the drug treated groups. Four doses were used to determine each dose response curve and $ED_{50}$ (that does which inhibits writhing by 50%). The $ED_{50}$ values and their 95% fiducial limits were determined by a computer assisted probit analysis. The results of analgesic testing for compounds of formula (I) wherein n=0 are shown in Table I.

TABLE I

| | Mouse Acetylcholine-Bromide-Induced Abdominal Constriction Assay | | | |
|---|---|---|---|---|
| Compound of Example | A | $R^1$ | x | $ED_{50}$ |
| 1e | phenyl | 2,6-Cl$_2$ | 2 | 5 |
| 2e | " | 4-OC$_6$H$_5$ | 1 | 8 |
| 3e | " | 3-CH$_3$O | 1 | 40% at 30 mg/Kg |
| 4e | " | 2-I | 1 | 30 |
| 5e | " | 2-Br | 1 | 23 |
| 6c | " | — | 0 | 15 |

Based on the above results, compounds of formula (I) of the invention may be used to treat mild to moderately severe pain in warm-blooded animals such as humans in a manner similar to the use of meperidine hydrochloride by administration of an analgesically effective dose. The dosage range would be from about 30 to 400 mg, in particular about 30 to 80 mg to about 300 to 400 mg, of active ingredient 1 to 4 times per day for an average (70 kg) human although it is apparent that activity of individual compounds of the invention will vary as will the pain being treated.

To prepare the pharmaceutical compositions of this invention, one or more compounds or salt thereof of Formula (I), including those wherein n=0, A=phenyl and x=0 or wherein x=1 and $R^1$=emthoxy at the 4-position, as the active ingredient, is intimately admixed with a pharmaceutical compounding techniques, which carrier may take a wide variety of forms depending on the form of administration, e.g., oral or parenteral such as intramuscular. For oral dosage forms, any of the usual pharmaceutical media may be employed. Thus, for liquid oral preparations, such as suspensions, elixirs and solutions, suitable carriers and additives include water, glycols, oils, alcohols, flavoring agents, preservatives, coloring agents and the like; for solid oral preparations such as powders, capsules and tablets, suitable carriers and additives include starches, sugars, diluents, granulating agents, lubricants, binders, disintegrating agents and the like. Because of their ease in administration, tablets and capsules with solid carriers represent the most advantageous oral dosage unit form. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient.

In the following Examples and throughout the specification, the following abbreviations may be used: mg (milligrams); g (grams); kg (kilograms); ml (milliliters); psi (pounds per square inch); mp (melting point); Et (ethyl); E (trans); Z (cis); Et$_2$O (diethylether); EtOH (ethanol); p.o. (per os, orally); i.p. (intraperitoneal); hr (hours); N (normal); min (minutes); and C,H,N,O, etc. (the chemical symbols for elements). Unless otherwise indicated, all temperatures are reported in °C. (degrees centigrade) and all references to ether are to Et$_2$O.

EXAMPLE 1 a.

2,6-Dichloro-[2-(3-hydroxypropyl)-1-piperidinyl]-benzeneacetonitrile

A 15 g (0.086 mole) sample of 2,6-dichlorobenzaldehyde was added to a solution of 15.4 g (0.086 mole) of 3-(2-piperidine)-1-propanol hydrochloride and 4.6 g (0.094 mole) of sodium cyanide in 100 mL of distilled water, and the reaction mixture stirred mechanically in a Morton flask for two days at room temperature. The mixture was extracted with ether, and the ether layer was washed with brine, dried (MgSO$_4$), and the ether evaporated in vacuo. There was obtained 29.7 g of the crude title compound as an oil.

b.

2-[1-[(Cyano)(2,6-dichlorophenyl)methyl]-2-piperidinyl]propyl-4-methylbenzenesulfonate A 16.3 g (0.085 mole) sample of p-toluenesulfonyl chloride was added in portions over 45 min to a cooled solution of 29.7 g of the crude product of Example 1a in 29 mL of dry pyridine so that the temperature was maintained between 0 and 5° C. The mixture was stirred with cooling for a total of 2.25 h, and ice and ether added. The ether layer was washed with 3N hydrochloric acid, dried (MgSO$_4$), and then the ether was evaporated in vacuo to give the title compound as a yellow oil.

c.

4-Cyano-4-(2,6-dichlorophenyl)octahydro-2H-quinolizine

The entire crude product obtained from Example 1b in 150 mL of dry DMF was added dropwise to a suspension of 0.088 mole of sodium hydride (from 4.2 g of 50% sodium hydride from which the oil had been washed with hexane) with stirring at room temperature under N$_2$. The reaction mixture was stirred at room temperature overnight. Water was added to the reaction mixture, and the mixture was extracted with ether. The ether layer was washed with brine, dried (MgSO$_4$), and the ether evaporated in vacuo to give 19.4 g of an oil (73% overall yield from the product of Example 1a) of the title compound.

d.

4-(2,6-dichlorophenyl)-1,2,3,6,7,8,9,9a-octahydroquinolizinium perchlorate (Formula (V): A=phenyl; R$^1$=Cl; x=2; n=0; Y$^-$=ClO$_4^-$)

A 5.4 mL (0.063 mole) sample of 70% aqueous perchloric acid was added to a solution of 19.4 g (0.063 mole) of the product of Example 1c in 100 mL of absolute ethanol. The atmosphere over the reaction was flushed with nitrogen into a sodium hypochlorite trap. The reaction mixture was stirred at room temperature for three days. Then the ethanol was evaporated in vacuo to give the title compound as an oil.

e.

trans-4-(2,6-dichlorophenyl)octahydro-2H-quinolizine perchlorate (Formula (I): A=phenyl; R$^1$=Cl; x=2; n=0)

A 15.8 g (0.25 mole) sample of sodium cyanoborohydride was added in portions to a solution of the crude oil from Example 1d in 150 mL of methanol. Methanolic hydrogen chloride was added until the pH stayed at 3 with nitrogen flowing over the reaction into a sodium hypochlorite trap. The reaction mixture was stirred at room temperature for 18 hr. The mixture was then acidified by the dropwise addition of concentrated hydrochloric acid, and stirred until the bubbling ceased. The mixture was then made basic with 3N sodium hydroxide, and extracted with ether. The ether layer was dried (K$_2$CO$_3$), and evaporated in vacuo to an oil. The oil was flash chromatographed on SiO$_2$ using 98% hexane, 2% ethyl acetate as the eluant. The first major compound bearing fractions were combined, and the solvent evaporated to give 3.5 g of an oil. The oil was treated with 70% aqueous perchloric acid and the white solid washed with ether. The salt was recrystallized from absolute ethanol to give 1.87 g (8.1%) yield of the title compound as a white solid, mp 203° C. dec.

EXAMPLE 2 a.

4-Phenoxy-[2-(3-hydroxypropyl)-1-piperidinyl]benzeneacetonitrile

An 11 g (0.556 mole) sample of 4-phenoxybenzaldehyde was added to a solution of 10 g (0.0556 mole) of 3-(2-piperidine)-1-propanol hydrochloride and 3.98 g (0.062 mole) of potassium cyanide in 100 mL of distilled water, and the reaction mixture was stirred in a Morton flask for two days at room temperature. The aqueous layer was decanted off and the organic layer dissolved in 50 mL of methanol. A sample of 5 g (0.028 mole) of 3-(2-piperidine)-1-propanol hydrochloride and 2 g (0.03 mole) of potassium cyanide were added to the reaction solution in methanol and allowed to stir for 18 hr. at room temperature. Then the reaction mixture was partitioned between water and ether. The ether layer dried (K$_2$CO$_3$), and the ether evaporated in vacuo to give 17.8 g (91% yield) of the crude title compound as an oil.

b.

2-[1-[(Cyano)(4-phenoxyphenyl)methyl]-2-piperidinyl]4-methylbenzenesulfonate

A 9.6 g (0.051 mole) sample of p-toluenesulfonyl chloride was added in portions over 30 min to a cooled solution of 17.8 g (0.051 mole) of the crude product of Example 2a in 16.4 mL of dry pyridine so that the temperature was maintained between −3° and −5° C. The reaction mixture was stirred with cooling for three hours keeping the temperature below 0° C. Then ice and ether were added to the reaction mixture. The ether layer was washed with 3N hydrochloric acid, dried c.
4-Cyano-4-octahydro-(4-phenoxyphenyl)-2H-quinolizine

A 15.6 g (0.032 mole) sample of the crude product of Example 2b in 100 mL of dry DMF was added in portions to a suspension of 0.035 mole of sodium hydride (from 1.69 g of 50% sodium hydride from which the oil had been removed by washing with hexane) with stirring at room temperature under nitrogen overnight. Water was then added to the reaction mixture, and the aqueous mixture extracted with ether. The ether layer was washed with brine, dried (MgSO$_4$), and the ether evaporated in vacuo to give 7.2 g (68% yield) of the crude title compound as an oil.

d.
4-Octahydro-(4-phenoxyphenyl)-1,2,3,6,7,8,9,9a-quinolizinium perchlorate (Formula V: A=phenyl;R$^1$=OC$_6$H$_5$;x=1;n=0;Y$^-$=-ClO$_4^-$)

A 1.73 mL (0.02 mole) sample of 70% aqueous perchloric acid was added to a solution of 6.7 g (0.02 mole) of the crude product of Example 2c in 150 mL of absolute ethanol. The atmosphere over the reaction was flushed with nitrogen into a sodium hypochlorite trap. The reaction mixture was stirred at room temperature overnight. The title compound, a white crystalline salt, (2.51 g) was collected (31% yield).

e.
trans-Octahydro-4-(4-phenoxyphenyl)-2H-quinolizine Hydrochloride (Formula (I): A=phenyl; R$^1$=OC$_6$H$_5$; x=1; n=0)

A 2.51 g (0.006 mole) sample of the product of Example 2 was partitioned between 10% sodium hydroxide and ether. The ether layer was dried (K$_2$CO$_3$), and the ether evaporated in vacuo to 2.19 g of a brown oil. The oil was dissolved in 60 mL of glacial acetic acid and 50 mg of platinum oxide added. The mixture was hydrogenated on a Paar apparatus at a pressure of 50 psi of hydrogen. After 1.25 h, the drop in pressure of hydrogen was 4.2 psi. The reaction mixture was filtered, and the acetic acid evaporated in vacuo to give an oily residue. The oil was made basic with 3N sodium hydroxide, and extracted with ether. The ether layer was dried (K$_2$CO$_3$), and the ether evaporated in vacuo to a yellow oil. The oil was treated with ethereal hydrogen chloride, and the salt recrystallized from acetonitrile to give 1.1 g (52% yield) of the title compound, mp 242.5°-244° C.

EXAMPLE 3
a.
3-Methoxy-α-[2-(3-hydroxypropyl)-1-piperidinyl]benzeneacetonitrile A 13.6 g (0.1 mole) sample of m-anisaldehyde was added to a solution of 18 g (0.1 mole) of 3-(2-piperidine)-1-propanol hydrochloride and 7.2 g (0.11 mole) of potassium cyanide in 100 mL of distilled water, and the reaction mixture was stirred mechanically in a Morton flask at room temperature for three days. The reaction mixture was extracted with ether. The ether layer was washed with brine, dried (K$_2$CO$_3$), and the ether evaporated to give 25.9 g (90% yield) of the crude title compound as an orange oil.

b.
2-[1-[(Cyano)(3-methoxyphenyl)methyl]-2-piperidinyl]-propyl-4-methylbenzenesulfonate A 13.4 g (0.071 mole) sample of p-toluenesulfonyl chloride was added in portions over 30 min to a cooled solution of 20.2 g (0.071 mole) of the crude product of Example 3a in 23 mL of dry pyridine under nitrogen and the temperature of the reaction mixture was maintained between 0 and −4° C. After stirring the reaction mixture for three hours, ether and ice were added to the reaction mixture. The red ether layer was washed with 3N hydrochloride acid, the resultant orange colored ether solution was dried (MgSO$_4$), and the ether evaporated in vacuo to give 25.6 g (79% yield) of the crude title compound as an oil.

c.
4-Cyano-4-(3-methoxyphenyl)octahydro-2H-quinolizine

A 25.6 g (0.055 mole) sample of the crude product of Example 3b in 200 mL of dry DMF was added in portions to a suspension of 0.056 mole of sodium hydride (from 2.7 g of 50% sodium hydride from which the oil had been washed with hexane) with stirring at room temperature under nitrogen overnight. Water was then added to the reaction mixture, and the aqueous mixture extracted with ether. The ether layer was washed with brine, dried (MgSO$_4$), and the ether evaporated in vacuo to give 15.4 g (80% yield) of the crude title compound as an oil.

d.
4-(3-methoxyphenyl)-1,2,3,6,7,8,9,9a-octahydroquinolizinium Perchlorate (Formula (V): A=phenyl;R$^1$=OCH$_3$;x=1;n=0;Y$^-$=-ClO$_4^-$)

A 4.9 mL (0.057 mole) sample of 70% aqueous perchloric acid was added to a solution of 15.4 g (0.057 mole) of the crude product of Example 3c in 150 mL of absolute ethanol. The atmosphere over the reaction was as flushed with nitrogen into a sodium hypochlorite trap. The solution was cooled with scratching to give 13.2 g (63% yield) of the crude perchlorate salt of 4-cyano-4-(3-methoxyphenyl) octahydro-2H-quinolizine. A 10 g (0.027 mole) sample of this perchlorate salt was dissolved in 100 mL of absolute ethanol and 125 mL of methanol by heating to boiling, and the solution was refluxed for 7 h with flushing under nitrogen into a sodium hypochloride trap. Then the solution was cooled and allowed to stand at 5° C. overnight. The white solid precipitate was filtered to give 8.6 g (93% yield) of the crude title compound, mp 154.5°-157° C.

e.
trans-Octahydro-4-(3-methoxyphenyl)-2H-quinolizine Hydrochloride (Formula (I): A=phenyl; R$^1$=OCH$_3$; x=1; n=0)

A 8.6 g (0.025 mole) sample of the product of Example 3d was partitioned between 10% sodium hydroxide and ether. The ether layer was washed with brine, dried (MgSO$_4$), and the ether evaporated in vacuo to give 6.5 of an oil. The oil was dissolved in 60 mL of glacial acetic acid and 130 mg of platinum oxide was added to the solution. The mixture was placed on the Paar apparatus at a pressure of 50 psi of hydrogen and allowed to run overnight. The drop in hydrogen pressure was 16 psi. The reaction mixture was filtered, and the acetic acid evaporated in vacuo to an oil residue. The oil was made basic with 3N sodium hydroxide, and extracted with ether. The ether layer was dried ($K_2CO_3$), and the ether evaporated in vacuo to a white oil. The oil was treated with ethereal hydrogen chloride, and the salt recrystallized from acetonitrile to give 4.5 g (64% yield) of the title compound as a white crystalline solid, mp 221°–223.5° C.

EXAMPLE 4 a.
2-Iodo-α-[2-(3-hydroxypropyl)-1-piperidinyl]benzeneacetonitrile

A 12.9 g (0.055 mole) sample of 2-iodobenzaldehyde was added to a solution of 10.8 g (0.06 mole) of 3-(2-piperidine)-1-propanol hydrochloride and 3.2 g (0.066 mole) of sodium cyanide in 100 mL of water and the mixture stirred in a Morton flask overnight at room temperature. The reaction mixture was extracted with ether. The ether layer was dried ($MgSO_4$), and the ether evaporated to give 19.9 g (86% yield) of the crude title compound as a yellow oil.

b.
2-[1-[(Cyano)(2-iodophenyl)methyl]-2-piperidinyl]propyl-4-methylbenzenesulfonate A 9.9 g (0.052 mole) sample of p-toluenesulfonyl chloride was added portionwise over a 1 hr period to a cooled solution of 19.9 g (0.052 mole) of the crude product of Example 4a in 17 mL of dry pyridine under nitrogen at 0° C. and allowed to stir at this temperature for three hours. Then ice and ether were added to the reaction mixture. The ether layer was washed with 3N hydrochloric acid, dried ($MgSO_4$), and the ether evaporated in vacuo to give 24.9 g (88% yield) of the crude title compound as a yellow oil.

c. 4-Cyano-4-octahydro-(2-iodophenyl)-2H-quinolizine

A 24.9 g (0.046 mole) sample of the crude product of Example 4b in 200 mL of dry DMF was added in portions to a suspension of 0.046 mole of sodium hydride (from 2.2 g of 50% sodium hydride from which the oil was removed by washing with hexane). The mixture was stirred at room temperature under nitrogen overnight. Water was added to the reaction mixture, and then the mixture was extracted with ether. The ether layer was dried ($MgSO_4$), and the ether evaporated in vacuo to give 21.1 g of the crude title compound as an oil.

d.
4-Octahydro-(2-iodophenyl)-1,2,3,6,7,8,9,9a-quinolizinium perchlorate (Formula (V): A=phenyl; $R^1$=I; x=1; n=0; $Y^-$=-$ClO_4^-$)

A 4.48 mL (0.052 mole) sample of 70% aqueous perchloric acid was added to a suspension of 21.1 g of the crude product of Example 4c in 200 mL of absolute ethanol. The atmosphere over the reaction was flushed with nitrogen into a sodium hypochlorite trap. The reaction mixture was stirred at room temperature overnight. The mixture was then allowed to stand in the refrigerator for two days. A 6.1 g sample of white solid was collected by filtration. This solid was dissolved in 150 mL of absolute methanol and the solution refluxed with stirring for four hours. Then the methanol was evaporated in vacuo, and the solid residue dissolved in absolute ethanol. The mixture was evaporated in vacuo to give 5.56 g (29% yield from the product of Example 4b) of the crude title compound.

e. trans-Octahydro-4-(2-iodophenyl)-2H-quinolizine Hydrochloride (Formula (I): A=phenyl; $R^1$=I; x=1; n=0)

A 5.2 g (0.015 mole) sample of the product of Example 4d was made basic with 3N sodium hydroxide and the aqueous mixture extracted with ether. The ether layer was dried ($Na_2SO_4$), and the ether evaporated in vacuo to give 4 g of a yellow oil. The oil was dissolved in 4.0 mL of glacial acetic acid and 80 mg of platinum oxide added to the solution. The mixture was placed on the Paar apparatus at a pressure of 53 psi and allowed to run for 18 h. The drop in pressure of hydrogen was 9 psi. The reaction mixture was filtered, and the acetic acid evaporated in vacuo to an oil. The oil was made basic with 3N sodium hydroxide, and extracted with ether. The ether layer was dried ($MgSO_4$), and the ether evaporated in vacuo to an oil. This oil was flash chromatographed on $SiO_2$ using 80% hexane, 20% acetone as the eluant. The first major compound bearing fractions were pooled and the solvent evaporated in vacuo to give 2.6 g (51% yield) of an oil. This oil was treated with ethereal hydrogen chloride and the salt recrystallized from acetonitrile to give 1.71 g (30% yield) of the title compound, mp 230°–233° C.

EXAMPLE 5 a.
2-Bromo-α-[2-(3-hydroxypropyl)-1-piperidinyl]benzeneacetonitrile

A 11.7 g (0.1 mole) sample of 2-bromobenzaldehyde was added to a solution of 17.7 g (0.1 mole) of 3-(2-piperidine)-1-propanol hydrochloride and 8.12 g (0.125 mole) of potassium cyanide in 55 mL of water and the mixture stirred overnight under nitrogen at room temperature. Then the reaction mixture was partitioned between water and ether. The ether layer was washed with brine, dried ($K_2CO_3$), and the ether evaporated in vacuo to give 35.8 g of the crude title compound as a yellow oil.

b.
2-[1-[(Cyano)(2-bromophenyl)methyl]-2-piperidinyl]propyl-4-methylbenzenesulfonate A 19 g (0.1 mole) sample of p-toluenesulfonyl chloride was added to a solution of 33.6 g (0.1 mole) of the crude product of Example 5a in 35 mL of dry pyridine and stirred at 10° C. for three hours. The reaction mixture was then partitioned between water and ether, and the ether layer was then washed with 3N hydrochloric acid and dried ($MgSO_4$). The ether solution was further washed with aqueous N,N-dimethylaminopropylamine, 3N hydrochloric acid, brine, and aqueous sodium bisulfite solution. The ether solution was then dried ($MgSO_4$), and the ether evaporated in vacuo to 35.1 g (71% yield) of the crude title compound as a yellow oil.

c.
4-Cyano-4-(2-bromophenyl)octahydro-2H-quinolizine

A 35.1 g (0.071 mole) sample of the crude product of Example 5b in 200 mL of dry DMF was added in portions to a suspension of 0.071 mole of sodium hydride (from 3.43 g of 50% sodium hydride washed free of oil with hexane) in 50mL of dry DMF. The reaction mixture was stirred for three hours under nitrogen at room temperature. Then water was added, and the aqueous mixture was extracted with ether. The ether layer was washed with water then brine, and dried (MgSO₄). The ether was evaporated in vacuo to give 20.7 g (91.6% yield) of the crude title compound as an oil.

d. 4-(2-Bromophenyl)-1,2,3,6,7,8,9,9a-octahydroquinolizinium Perchlorate (Formula (V): A=phenyl; R¹=Br; x=1; n=0; Y⁻=ClO₄⁻)

A 5.4 mL (0.0628 mole) sample of 70% aqueous perchloric acid was added to a solution of 20 g (0.0628 mole) of the crude product of Example 5c in 100 mL of absolute ethanol. The atmosphere over the reaction was flushed with nitrogen into a sodium hypochlorite trap. After stirring the solution for two hours, ether was added to give 17.7 g (74% yield) of the title compound as a white solid, mp 125°-126° C.

e. trans-4(2-Bromophenyl)octahydro-2H-quinolizine Hydrochloride (Formula (I): A=phenyl; R¹=Br; x=1; n=0)

A 3.78 g sample (0.01 mole) of 4-(2-bromophenyl)-1,2,3,6,7,8,9,9a-octahydroquinolizinium perchlorate, the product of Example 5d, was partitioned between ether and sodium hydroxide solution. The ether layer was washed with brine, dried (K₂CO₃) and the ether evaporated under reduced pressure. The residue (2.0 g) was hydrogenated in 25 mL of glacial acetic acid over 50 mg of PtO₂ at 50 psi in a Parr shaker. After 15 minutes, the hydrogen uptake was complete. The catalyst was removed by filtration and the solvent was evaporated under reduced pressure. The residue was partitioned between ether and sodium hydroxide and dried (K₂CO₃). The residue was taken up in ether and ethereal hydrogen chloride added. The precipitate was recrystallized from 2-propanol-ether to give 1.09 g (33% yield) of the title compound as a white solid, mp 242°-246° C.

EXAMPLE 6 a. Ethyl-4-(2-pyridyl)-2-benzoylbutyrate

A sample of 120 g (0.62 mole) of ethyl benzoylacetate was added to 1.44 g (0.062 mole) of sodium and 32.8 g (0.31 mole) of 2-vinylpyridine added under an atmosphere of nitrogen. The mixture was heated with mechanical stirring on the steam bath for 17 h. After cooling the reaction mixture to room temperature, 100 mL of 3N hydrochloric acid was added, and the aqueous mixture washed with ether. The hydrochloric acid layer was made basic with 10% potassium carbonate solution, and extracted with ether. The ether layer was washed with brine, dried (MgSO₄), and the ether evaporated in vacuo to give 83.4 g (90% yield) of the crude title compound as a red oil.

b. 2-(3-Benzoyl)propylpyridine

A sample of 57.3 g (0.192 mole) of the product of Example 6a was added to 56 mL of concentrated hydrochloric acid and heated for 2 hr on a steam bath. The mixture was then cooled to room temperature, and then made basic with saturated potassium carbonate solution, and the aqueous mixture extracted with ether. The ether layer was washed with brine, dried (K₂CO₃) and the ether evaporated in vacuo to give 44.7 g of a red oil.

The oil was distilled under vacuum to give 40.6 g (94% yield) of the title compound as a yellow oil (Bp 135°-140° C. at 0.12 mm Hg).

c. Octahydro-4-phenyl-2H-quinolizine Hydrochloride (Formula (I): A=phenyl; x=0; n=0)

A 20 g (0.089 mole) sample of the product of Example 6b was dissolved in 200 mL of glacial acetic acid and 0.4 g of platinum oxide was added. The mixture was placed on a Parr apparatus at a pressure of 60 psi of hydrogen and after 13.5 hours, there was a 32.5 psi decrease in hydrogen pressure. The reaction mixture was filtered, and the acetic acid evaporated in vacuo to an oil. The oil was made basic with saturated potassium carbonate solution, and extracted with methylene chloride. The methylene chloride layer was washed with brine, dried (K₂CO₃), and the methylene chloride evaporated in vacuo to give 19 g of an oil. The oil was dissolved in acetonitrile and treated with ethereal hydrogen chloride to give 13.2 g of salt as a white solid. The salt was recrystallized from methanol-acetonitrile to give 9.4 g (60% yield) of the title compound as a white solid, mp 268°-269° C.

What is claimed is:

1. An octahydroquinolizine of the following formula (I)

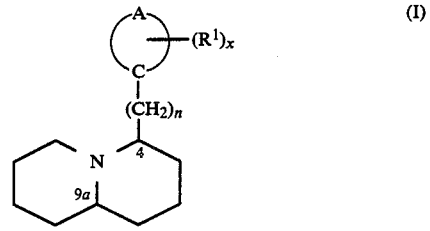

wherein

A represents the atoms necessary to form a phenyl, naphthyl, cycloalkyl, or cycloalkenyl ring system as the A-C cycle shown in formula (I);

R¹ is independently cyano; halogen; alkyl; phenoxy; alkylthio; phenylthio; phenylthio substituted by acetamido, halo, or alkyl; haloalkyl; alkenyl; alkynyl or cycloalkenyl;

n is the integer 0; and x is the integer 0, 1, 2, or 3, provided that when A is phenyl, x is 1, 2, or 3; and, when A is phenyl, x is 1, and R¹ is methoxy, R¹ is in the 2- or 3-position of the phenyl ring;

wherein said cycloalkyl and cycloalkeny are of C₃-C₇ atoms, and the alkyl portion of all the alkyl alkenyl and alkynyl containing groups are lower alkenyl, alkenyl or alkyl; and the pharmaceutically-acceptable acid-addition salts thereof.

2. The octahydroquinolizine of claim 1, wherein said cycloalkyl for A is cycloalkyl of about 3 to 7 carbons; said cycloalkenyl for A is cycloalkenyl of about 3 to 7 carbons; said halogen for R¹ and for substitution on phenylthio for R¹ is fluoro, chloro, bromo, or iodo; the alkyl portion of said alkyl, alkylthio and haloalkyl for R¹ is of about 1 to 8 carbons; said alkyl substituted on said phenylthio is of about 1 to 6 carbons; said alkenyl for R¹ is of about 2 to 8 carbons; said alkynyl for R¹ is of about 2 to 8 carbons; the halo portion of said haloalkyl for R¹ is one or more of fluoro, chloro, bromo, or iodo atoms; and said cycloalkenyl for R₁ is cycloalkenyl of 3 to 7 carbons.

3. The octahydroquinolizine of claim 1, wherein the 4-position substituent and the 9a-position hydrogen of formula (I) are trans to each other.

4. The octahydroquinolizine of claim 3, wherein said octahydroquinolizine is the (+) isomer.

5. The octahydroquinolizine of claim 3, wherein said octahydroquinolizine is the (−) isomer.

6. The octahydroquinolizine of claim 1, wherein A represents the atoms necessary to form a phenyl ring.

7. The octahydroquinolizine of claim 6, wherein at least one $R^1$ group is at the ortho position of the phenyl ring.

8. The octahydroquinolizine of claim 1, wherein said octahydroquinolizine is selected from the group consisting of:
4-(2,6-dichlorophenyl)octahydro-2H-quinolizine;
octahydro-4-(4-phenoxyphenyl)-2H-quinolizine;
octahydro-4-(2-iodophenyl)-2H-quinolizine; and,
4-(2-bromophenyl)octahydro-2H-quinolizine,
or a pharmaceutically-acceptable acid-addition salt thereof.

9. The octahydroquinolizine of claim 8, wherein the 4-position substituent and the 9a-position hydrogen are trans to each other.

10. The octahydroquinolizine of claim 1, which is trans-octahydro-4-(4-phenoxyphenyl)-2H-quinolizine or a pharmaceutically-acceptable acid-addition salt thereof.

11. A pharmaceutical composition effective in the treatment of pain which comprises a pharmaceutically-acceptable carrier and a pain-reducing amount of an octahydroquinolizine of the following formula (I):

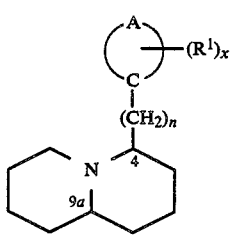

(I)

wherein
A represents the atoms necessary to form a phenyl, naphthyl, cycloalkyl, or cycloalkenyl ring system as the A-C cycle shown in formula (I);
$R^1$ is independently cyano; halogen; alkyl; phenoxy; alkylthio; phenylthio; phenylthio substituted by acetamido, halo, or alkyl; haloalkyl; alkenyl; alkynyl or cycloalkenyl;
n is the integer 0; and
x is the integer 0, 1, 2, or 3,
and the pharmaceutically-acceptable acid-addition salts thereof.

12. The pharmaceutical composition of claim 11, wherein said cycloalkyl for A is cycloalkyl of about 3 to 7 carbons; said cycloalkenyl for A is cycloalkenyl of about 3 to 7 carbons; said halogen for $R^1$ and for substitution on phenylthio for $R^1$ is fluoro, chloro, bromo, or iodo; the alkyl portion of said alkyl, alkylthio and haloalkyl for $R^1$ is of about 1 to 8 carbons; the alkenyl portion of said alkenyl for $R^1$ is of about 2 to 8 carbons, the alkynyl portion of said alkynyl for $R^1$ is of about 2 to 8 carbons; the halo portion of said haloalkyl for $R^1$ is one or more of fluoro, chloro, bromo, or iodo atoms; and said cycloalkenyl for $R^1$ is cycloalkenyl of 3 to 7 carbons.

13. The pharmaceutical composition of claim 11, wherein the 4-position substituent and the 9a-position hydrogen are trans to each other.

14. The pharmaceutical composition of claim 11, wherein said octahydroquinolizine is selected from the group consisting of:
4-(2,6-dichlorophenyl)octahydro-2H-quinolizine;
octahydro-4-(4-phenoxyphenyl)-2H-quinolizine;
octahydro-4-(2-iodophenyl)-2H-quinolizine;
4-(2-bromophenyl)octahydro-2H-quinolizine;
octahydro-4-phenyl-2H-quinolizine; and,
4(4-methoxyphenyl)octahydro-2H-quinolizine,
or a pharmaceutically-acceptable acid-addition salt thereof.

15. An octahydroquinolizinium salt of the following formula (Va):

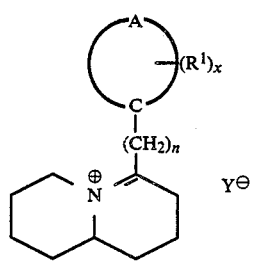

(Va)

wherein
A represents the atoms necessary to form a phenyl, naphthyl, cycloalkyl, or cycloalkenyl ring system as the A-C cycle shown in formula (I);
$R^1$ is independently cyano; halogen; alkyl; phenoxy; alkylthio; phenylthio; phenylthio substituted by acetamido, halo, or alkyl; haloalkyl; alkenyl; alkynyl or cycloalkenyl; wherein said cycloalkyl and cycloalkenyl are of $C_3$–$C_7$ atoms, and the alkyl portion of all the alkyl, alkenyl and alkynyl containing groups are lower alkenyl, alkynyl or alkyl
n is the integer 0;
x is the integer 0, 1, 2, or 3, provided that when A is phenyl, x is 1, 2, or 3; and
$Y^-$ is an anion.

16. The octahydroquinolizium salts of claim 15, wherein said anion is perchlorate, tetrafluoroborate, or trifluoromethanesulfonate.

17. The octahydroquinolizinium salt of claim 15, wherein said cycloalkyl for A is cycloalkyl of about 3 to 7 carbons; said cycloalkenyl for A is cycloalkenyl of about 3 to 7 carbons; said halogen for $R^1$ and for substitution on phenylthio for $R^1$ is fluoro, chloro, bromo, or iodo; the alkyl portion of said alkyl, alkylthio and haloalkyl for $R^1$ is of about 1 to 8 carbons; said alkyl substituted on said phenylthio is of about 1 to 6 carbons; said alkenyl for $R^1$ is of about 2 to 8 carbons; said alkynyl for $R^1$ is of about 2 to 8 carbons; the halo portion of said haloalkyl for $R^1$ is one or more of fluoro, chloro, bromo, or iodo atoms; and said cycloalkenyl for $R^1$ is cycloalkenyl of 3 to 7 carbons.

18. The octahydroquinolizinium salt of claim 15, wherein said octahydroquinolizinium salt is selected from the group consisting of:
4-(2,6-dichlorophenyl)-1,2,3,6,7,8,9,9a-octahydroquinolizinium perchlorate;

4-octahydro-(4-phenoxyphenyl)-1,2,3,6,7,8,9,9a-quinolizinium perchlorate;

4-octahydro-(2-iodophenyl)-1,2,3,6,7,8,9,9a-quinolizinium perchlorate; and, 4-(2-bromophenyl)-1,2,3,6,7,8,9,9a-octahydroquinolizinium perchlorate.

19. A method of relieving pain in a mammal which comprises administering to the mammal a pharmaceutical composition effective in the treatment of pain which comprises a pharmaceutically-acceptable carrier and a pain-reducing amount of an octahydroquinolizine of the following formula (I):

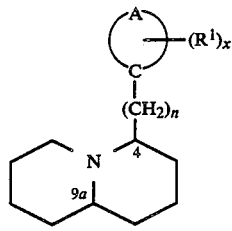

wherein

A represents the atoms necessary to form a phenyl, naphthyl, cycloalkyl, or cycloalkenyl ring system as the A-C cycle shown in formula (I);

$R^1$ is independently cyano; halogen; alkyl; alkyloxy; phenoxy; alkylthio; phenylthio; phenylthio substituted by acetamido, halo, or alkyl; haloalkyl; alkenyl; alkynyl or cycloalkenyl; wherein said cycloalkyl and cycloalkenyl are of $C_3$–$C_7$ atoms, and the alkyl, alkenyl and alkynyl portion of all the alkyl containing groups are lower alkenyl, alkynyl or alkyl;

n is the integer 0, 1, or 2; and x is the larger integer 0, 1, 2, or 3, and the pharmaceutically-acceptable acid-addition salts thereof.

20. The method of claim 19, wherein said cycloalkyl for A is cycloalkyl of about 3 to 7 carbons; said cycloalkenyl for A is cycloalkenyl of about 3 to 7 carbons; said halogen for $R^1$ and for substitution on phyenylthio for $R^1$ is fluoro, chloro, bromo, or iodo; the alkyl portion of said alkyl, alkyloxy, alkylthio and haloalkyl for $R^1$ is of about 1 to 8 carbons; said alkyl substituted on said phenylthio is of about 1 to 6 carbons; said alkenyl for $R^1$ is of about 2 to 8 carbons; said alkynyl for $R^1$ is of about 2 to 8 carbons; the halo portion of said haloalkyl for $R^1$ is one or more of fluoro, chloro, bromo, or iodo atoms; and said cycloalkenyl for $R^1$ is cycloalkenyl of 3 to 7 carbons.

* * * * *